(12) United States Patent
Baranes et al.

(10) Patent No.: US 10,695,364 B2
(45) Date of Patent: Jun. 30, 2020

(54) ANTI-HEMORRHAGING COMPOSITIONS

(71) Applicant: Ariel-University Research and Development Company Ltd., Ariel (IL)

(72) Inventors: Danny Baranes, Beer-Sheva (IL); Ayala Gancz, Alfe-Menashe (IL); Yekaterina Zuev, Ariel (IL); Liat Hammer, Modiln (IL)

(73) Assignee: Ariel-University Research and Development Company Ltd., Ariel (IL)

( * ) Notice: Subject to any disclaimer, the term of this patent is extended or adjusted under 35 U.S.C. 154(b) by 4 days.

(21) Appl. No.: 15/761,447

(22) PCT Filed: Sep. 20, 2016

(86) PCT No.: PCT/IL2016/051039
§ 371 (c)(1),
(2) Date: Mar. 20, 2018

(87) PCT Pub. No.: WO2017/046809
PCT Pub. Date: Mar. 23, 2017

(65) Prior Publication Data
US 2019/0076470 A1  Mar. 14, 2019

Related U.S. Application Data

(60) Provisional application No. 62/221,040, filed on Sep. 20, 2015.

(51) Int. Cl.
*A61K 33/10* (2006.01)
*A61K 31/194* (2006.01)
(Continued)

(52) U.S. Cl.
CPC ............ *A61K 33/10* (2013.01); *A61K 9/0014* (2013.01); *A61K 31/194* (2013.01); *A61K 35/614* (2013.01); *A61P 7/04* (2018.01)

(58) Field of Classification Search
None
See application file for complete search history.

(56) References Cited

U.S. PATENT DOCUMENTS

| | | | | |
|---|---|---|---|---|
| 5,985,315 A | * | 11/1999 | Patat | ...................... A61L 24/106 424/443 |
| 2001/0055621 A1 | * | 12/2001 | Baugh | ................. A61L 24/0005 424/530 |

FOREIGN PATENT DOCUMENTS

| WO | WO 2014/183886 | 11/2014 | |
|---|---|---|---|
| WO | WO-2014183886 A1 * | 11/2014 | ............... C12Q 1/56 |

(Continued)

OTHER PUBLICATIONS

International Preliminary Report on Patentability dated Mar. 29, 2018 From the International Bureau of WIPO Re. Application No. PCT/IL2016/051039. (8 Pages).

(Continued)

*Primary Examiner* — Carlos A Azpuru
*Assistant Examiner* — Casey S Hagopian

(57) ABSTRACT

Compositions comprising a citrate salt and a calcium carbonate-containing material, articles-of-manufacturing and kits comprising same and uses thereof for inducing blood coagulation and/or for reducing or arresting hemorrhaging, particularly internal hemorrhaging, are disclosed.

25 Claims, 5 Drawing Sheets
(5 of 5 Drawing Sheet(s) Filed in Color)

(51) Int. Cl.
*A61P 7/04* (2006.01)
*A61K 9/00* (2006.01)
*A61K 35/614* (2015.01)

(56) References Cited

FOREIGN PATENT DOCUMENTS

| WO | WO 2015/089626 | 6/2015 |
| WO | WO 2015/166497 | 11/2015 |
| WO | WO 2017/046809 | 3/2017 |

OTHER PUBLICATIONS

International Search Report and the Written Opinion dated Dec. 15, 2016 From the International Searching Authority Re. Application No. PCT/IL2016/051039. (14 Pages).
Mollison "The Introduction of Citrate as an Anticoagulant for Transfusion and of Glucose as a Red Cell Preservative", British Journal of Haematology, 108(1): 13-18, Jan. 31, 2000.
Supplementary European Search Report and the European Search Opinion dated Mar. 28, 2019 From the European Patent Office Re. Application No. 16845849.5. (7 Pages).
Communication Pursuant to Article 94(3) EPC dated Apr. 30, 2020 From the European Patent Office Re. Application No. 16845849.5. (5 Pages).

\* cited by examiner

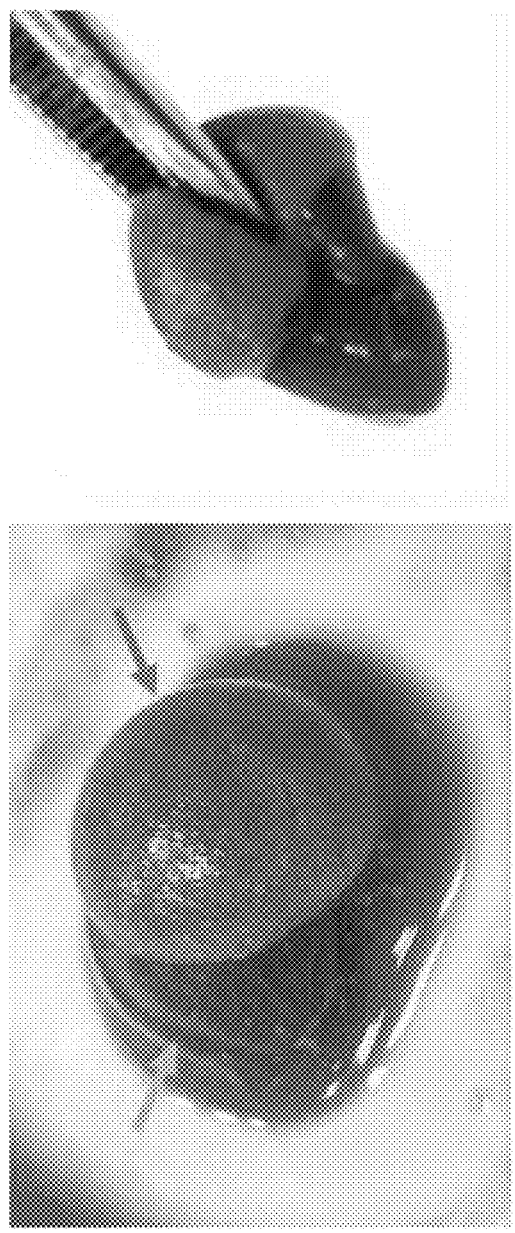
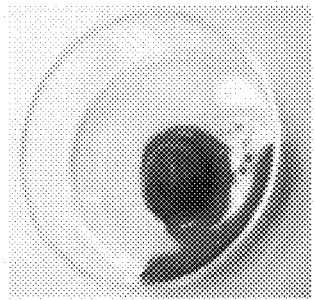
FIG. 2A  FIG. 2B  FIG. 2C
Citrate + Geological aragonite

ANTI-HEMORRHAGING COMPOSITIONS

RELATED APPLICATIONS

This application is a National Phase of PCT Patent Application No. PCT/IL2016/051039 having International filing date of Sep. 20, 2016, which claims the benefit of priority under 35 USC § 119(e) of U.S. Provisional Patent Application No. 62/221,040 filed on Sep. 20, 2015. The contents of the above applications are all incorporated by reference as if fully set forth herein in their entirety.

FIELD AND BACKGROUND OF THE INVENTION

The present invention, in some embodiments thereof, relates to medicine and, more particularly, but not exclusively, to novel compositions which are useful in inducing blood coagulation and/or in reducing or blocking hemorrhaging, for example, internal hemorrhaging.

Hemorrhaging, or bleeding, is a term used to describe a condition in which blood escapes from the circulatory system. Bleeding can occur internally, where blood leaks from blood vessels inside the body, or externally, either through a natural opening such as the mouth, nose, ear, urethra, vagina or anus, or through a break in the skin. By "internal hemorrhaging" it is meant that a blood vessel inside the body is injured and leaks. Blood leakage from internal blood vessels can be manifested also as external hemorrhaging, yet the injured blood vessel, which is the source of hemorrhaging, is internal.

Coagulation, also known as clotting, is the process by which liquid blood forms a clot. Coagulation may result in hemostasis, a term known to describe the cessation of blood loss from a damaged vessel. The mechanism of coagulation, as is well-described in the art, involves both activation, adhesion, and aggregation of platelets and deposition and maturation of fibrin.

An anti-hemorrhagic agent is a substance that promotes hemostasis and arrests bleeding, and is also referred to in the art as a hemostatic agent, a hemostat, or as a pro-coagulant.

Currently used anti-hemorrhagic agents can be categorized into systemic drugs, which act by inhibiting fibrinolysis or promoting coagulation; and locally-acting hemostatic agents, which act by causing vasoconstriction or promoting platelet aggregation.

Anti-hemorrhagic, or hemostatic, agents are typically used during surgical procedures to achieve hemostasis. Locally-acting hemostatic agents, however, have been gaining popularity for use in emergency bleeding control, particularly for internal hemorrhaging caused by severe trauma.

Exemplary known hemostats include microfibrillar collagen hemostat (MCH), which is a topical agent composed of resorbable microfibrillar collagen, typically used in surgical procedures; Chitosan hemostats, which are also topical agents composed of chitosan and its salts, act by bonding with platelets and red blood cells to form a gel-like clot which seals a bleeding vessel, and are known to be used to stop traumatic life-threatening bleeding; zeolites, such as the product QuikClot, act as absorbents, and are used for sealing severe injuries quickly; Thrombin and fibrin glue products are used surgically to treat bleeding and to thrombose aneurysms; desmopressin is used to improve platelet function by activating arginine vasopressin receptor 1A; Tranexamic acid and aminocaproic acid inhibit fibrinolysis, and lead to a de facto reduced bleeding rate. Some foam-forming agents have also been developed, which, once applied, form a foam that physically reduces bleeding by applying pressure to the blood vessels. The formed foam should thereafter be surgically removed.

Internal hemorrhaging (or bleeding) due to blunt or penetrating, civilian or military, trauma is known to cause major loss of human life, as well as drainage of hospital and blood bank resources. Among the most lethal injuries are civilian and military injuries that cause internal hemorrhaging.

Common traumas that lead to internal hemorrhaging include injuries of solid abdominal organs such as liver, spleen, kidneys and other organs. These injuries are commonly treated by surgical techniques such as suturing, resection and devascularization of the organ. A large number of liver, spleen and renal injuries do not respond to these techniques, leading to death of the patient or sacrifice of a valuable organ.

Moreover, sever internal hemorrhaging can lead to rapid and heavy loss of blood and death prior to the availability of the surgical treatment.

Blocking internal hemorrhaging by techniques which can be applied within a short time upon the injury is therefore highly sought for, with the goal being agents or compositions which can arrest massive internal bleeding within several minutes from the injury and preserve the blockage for at least a few hours, for example, until a surgical treatment can be provided to the injured subject (e.g., until the subject is brought to a hospital).

Citrate salts are known anti-coagulation agents. Some compositions containing a citrate salt in combination with pH-adjusting agents such as sodium bicarbonate, or sodium carbonate, have been described, in which the sodium carbonate or bicarbonate are used to prolong the anti-coagulation activity of citrate by maintaining a non-acidic pH.

WO 2015/166497, by the present assignee, describes that calcium carbonate, for example, in the form of aragonite extracted from the skeleton of the corals acts as an anti-coagulation or de-coagulation agent.

U.S. Pat. No. 5,985,315 describes a device for isolation of blood coagulation components using coral skeleton made of calcium carbonate. Some of the blood fractions passed through the device are described therein as human blood anti-coagulated by citrate.

SUMMARY OF THE INVENTION

The present inventors have now uncovered that by contacting blood with calcium carbonate, either crystalline (in various crystalline forms) or amorphous, and a citrate salt, fast coagulation of the blood is effected, and that blood clots formed thereby are preserved for several hours. These findings demonstrate that a composition containing calcium carbonate, either crystalline (in various crystalline forms) or amorphous, and a citrate salt, either as a ready-to-use composition or as a composition prepared during its application (by simultaneously or sequentially applying the calcium carbonate, either crystalline (in various crystalline forms) or amorphous, and the citrate salt, can be efficiently used in inducing blood coagulation and/or treating hemorrhage, while superseding, and circumventing limitations associated with, other known hemostatic agents or compositions.

According to an aspect of some embodiments of the present invention there is provided blood coagulation-inducing composition comprising a citrate salt and a calcium-carbonate containing material.

According to some of any of the embodiments described herein, the calcium carbonate-containing material comprises crystalline calcium carbonate.

According to some of any of the embodiments described herein, the calcium carbonate-containing material comprises a coral exoskeleton.

According to some of any of the embodiments described herein, the calcium carbonate-containing material comprises acellular coral exoskeleton.

According to some of any of the embodiments described herein, the calcium carbonate-containing material comprises aragonite.

According to some of any of the embodiments described herein, the calcium carbonate-containing material comprises biogenic aragonite.

According to some of any of the embodiments described herein, the calcium carbonate-containing material comprises geological aragonite.

According to some of any of the embodiments described herein, the calcium carbonate-containing material comprises amorphous calcium carbonate.

According to some of any of the embodiments described herein, the calcium carbonate-containing material is a particulate material.

According to some of any of the embodiments described herein, the particulate material comprises particles having an average particle diameter in the range of from 0.1 micron to 10 millimeter, or from 0.1 micron to 1 millimeter, or from 0.1 micron to 500 microns, or from 0.5 microns to 500 microns, or from 1 micron to 500 microns, or from 5.0 microns to 500 microns.

According to some of any of the embodiments described herein, a weight ratio of the citrate and the calcium carbonate-containing material ranges from 10:1 to 1:300. According to some of any of the embodiments described herein, the composition is formulated as a topical dosage form.

According to some of any of the embodiments described herein, the composition is in a form of a powder, a gel, a spray, a foam, a mousse, an ointment, a paste, a lotion, a gauze, a wound dressing, a suspension, an adhesive bandage, a non-adhesive bandage, a wipe, a gauze, a pad, and a sponge.

According to an aspect of some embodiments of the present invention there is provided an article-of-manufacturing comprising the composition of any of the respective embodiments, the article-of-manufacturing being configured to apply the composition to an injured blood vessel and/or tissue.

According to an aspect of some embodiments of the present invention there is provided a kit comprising the composition of any of the respective embodiments as described herein or the article-of-manufacturing of any of the respective embodiments as described herein.

According to some of any of the embodiments described herein, the kit is identified for use in inducing blood coagulation.

According to some of any of the embodiments described herein, the calcium carbonate-containing material and the citrate salt are packaged together within the kit.

According to some of any of the embodiments described herein, the calcium carbonate-containing material and the citrate salt are packaged individually within the kit.

According to an aspect of some embodiments of the present invention there is provided a method of inducing coagulation of blood, the method comprising contacting the blood with the composition of any of the respective embodiments described herein.

According to some of any of the embodiments described herein, the contacting is effected by means of the article-of-manufacturing of claim 14.

According to some of any of the embodiments described herein, at least 50% of the blood is clotted upon contacting with the composition for less than 10 minutes.

According to some of any of the embodiments described herein, at least 50% of the clotted blood remains clotted from at least 2 hours.

According to some of any of the embodiments described herein, the contacting is effected in vivo.

According to some of any of the embodiments described herein, the contacting is effected by applying the composition to an injured blood vessel.

According to some of any of the embodiments described herein, the blood vessel is an internal blood vessel.

According to some of any of the embodiments described herein, the blood vessel is of an internal tissue.

According to some of any of the embodiments described herein, the tissue is selected from a hepatic tissue, a renal tissue, an abdominal tissue, a pancreatic tissue, a gastrointestinal tissue, a pulmonary tissue, a gonadal tissue, a spleen tissue, a skin tissue, a vascular tissue, and nervous.

According to some of any of the embodiments described herein, the method is for reducing or arresting hemorrhaging in a subject in need thereof.

According to some of any of the embodiments described herein, the hemorrhaging is an internal hemorrhaging.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B:
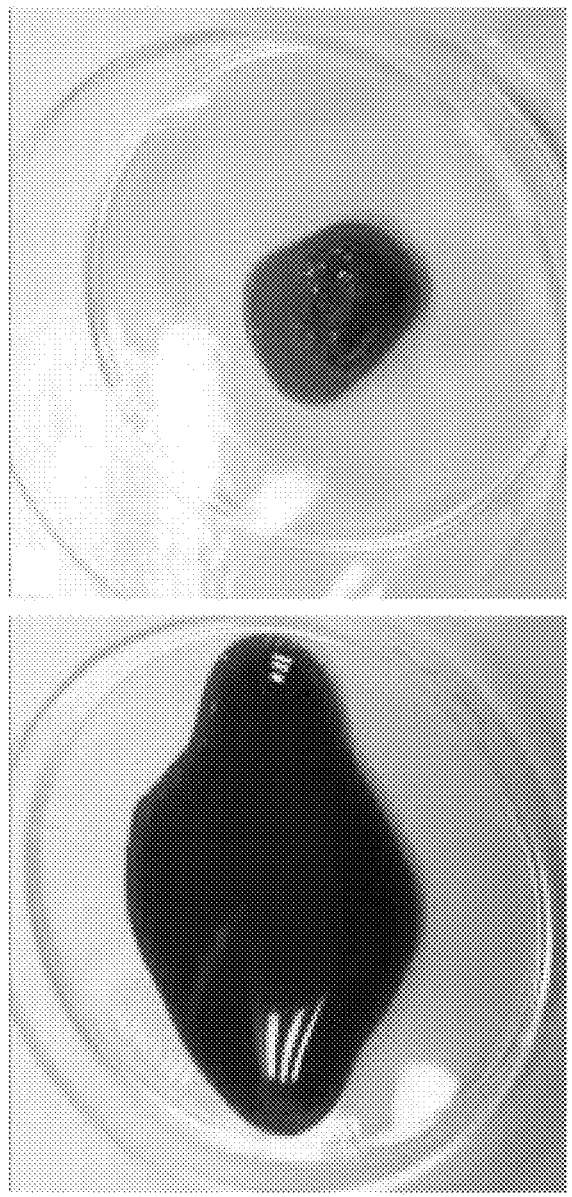
Figure 3:
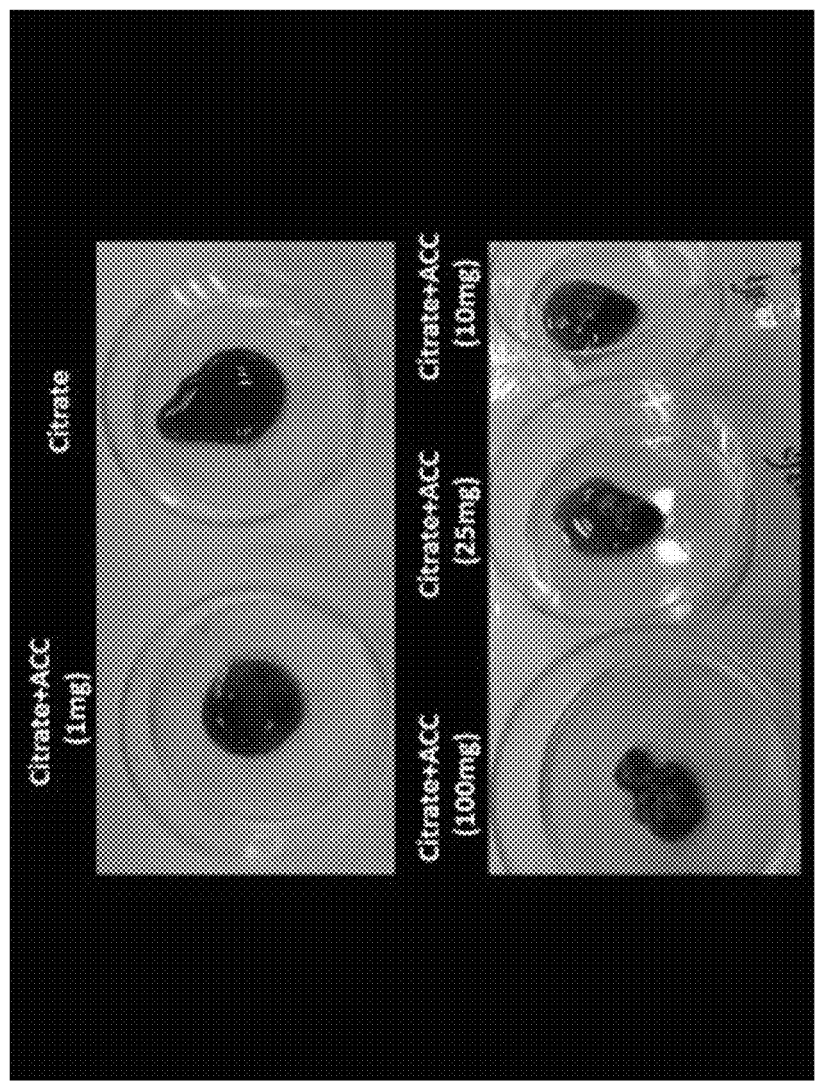
Figure 4:
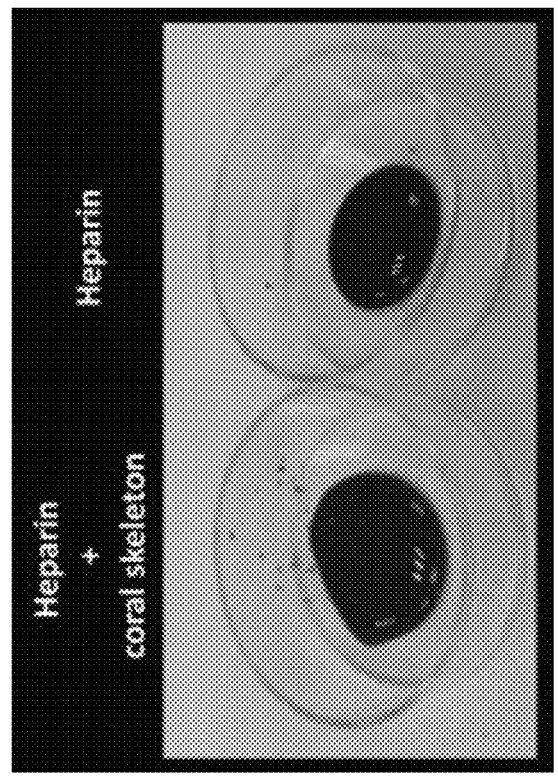
Figure 5:
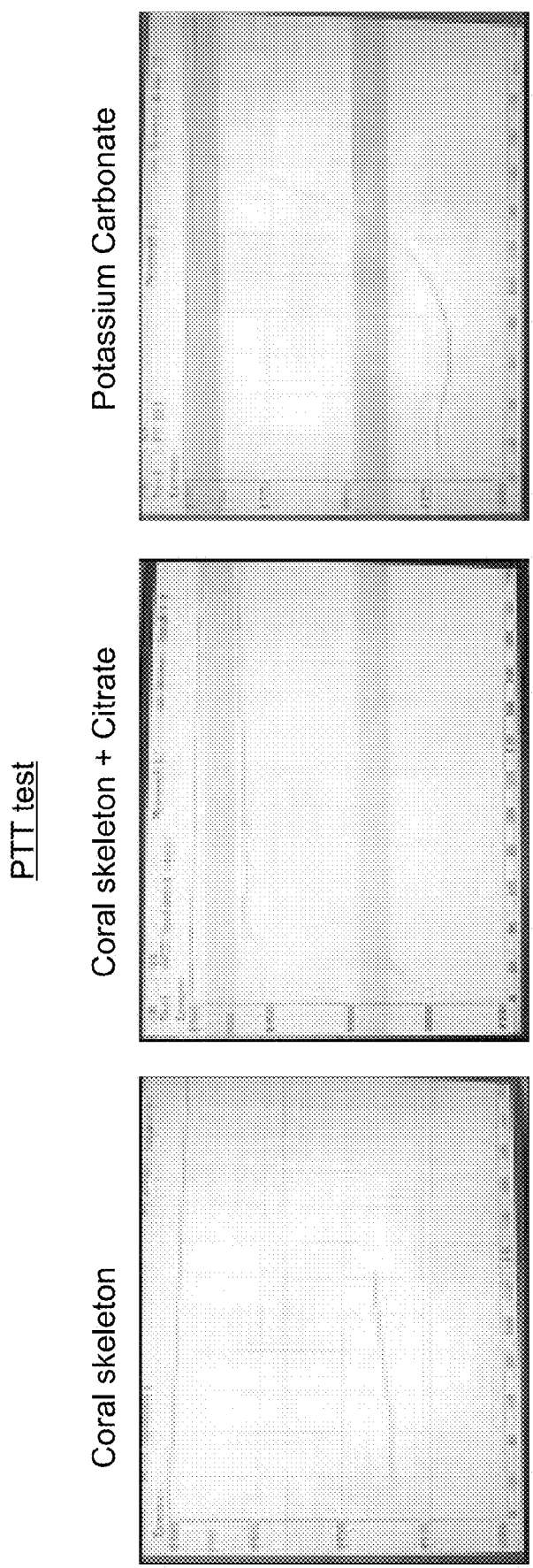

FIGS. 1A-B present images showing coagulation of blood drawn from mice in the presence of citrate (FIG. 1A) and by a combination of particulate coral skeleton and citrate (FIG. 1B);

FIGS. 2A-C present images showing blood jellification induced by geological aragonite and citrate;

FIG. 3 presents images showing blood coagulation induced by amorphous calcium carbonate and citrate in a dose-dependent manner;

FIG. 4 presents images showing that particulate coral skeleton does not induce coagulation when used with heparin; and FIG. 5 presents data obtained in a PTT assay conducted with a coral exoskeleton alone, a combination with a coral exoskeleton and citrate and with potassium carbonate, showing the fast coagulation induced by the combination of a coral exoskeleton and citrate.

DESCRIPTION OF SPECIFIC EMBODIMENTS OF THE INVENTION

The present invention, in some embodiments thereof, relates to medicine and, more particularly, but not exclusively, to novel compositions which are useful in inducing blood coagulation and/or in reducing or blocking hemorrhaging, for example, internal hemorrhaging.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

It has previously been uncovered by some of the present inventors that calcium carbonate-containing materials such as aragonite and/or calcium carbonate derived from coral skeleton, act as an anti-coagulant or de-coagulant of blood.

While further exploring the effect of exposing blood to calcium carbonate, the present inventors have uncovered, by serendipity, that when a calcium carbonate-containing material is contacted with blood in the presence of a citrate salt, induction of blood coagulation is effected.

As demonstrated in the Examples section that follows, the present inventors have uncovered that calcium carbonate of various origins, and of various crystalline (or amorphous) structures, exhibits the same effect on blood in the presence of citrate. Massive coagulation of blood was observed within few minutes and was preserved for several hours.

The features exhibited by the combination of calcium carbonate and citrate, taken together with the water insolubility of the calcium carbonate, are particularly useful for treating internal hemorrhaging, by providing an immediate, effective solution to internal hemorrhaging, including massive internal hemorrhaging, which can be applied at the place where trauma occurs, if needed, and which can be preserved until surgical or other more complicated procedures are applied.

Embodiments of the present invention therefore relate to a blood coagulation-inducing or an anti-hemorrhaging composition, and to uses thereof in inducing blood coagulation and in treating hemorrhaging, such as internal hemorrhaging, in a subject in need thereof.

The compositions disclosed herein are simple to use, provide an immediate solution also in cases of massive hemorrhaging, can be applied also by a non-professional user, and do not require excessive procedures such as surgical removal thereof.

The Composition:

According to an aspect of some embodiments of the present invention there is provided a composition comprising a citrate salt and a calcium-carbonate containing material.

The disclosed composition, in some embodiments, is a composition which is useful in inducing blood coagulation, and/or in reducing or arresting hemorrhaging, in a subject in need thereof. The composition is also referred to herein interchangeably as "an anti-hemorrhaging composition" or as "a blood coagulation-inducing composition".

Herein throughout, the term "hemorrhaging", which is also referred to herein as "bleeding", describes blood escape from the circulatory system. This term encompasses both internal and external bleeding. This term encompasses bleeding as a result of injury of a blood vessel or a tissue containing same. The blood vessel can be a part of an internal tissue or an external tissue, as described herein.

Herein throughout, the phrase "calcium carbonate-containing material" describes a material, a substance or a composition-of-matter, which is substantially consisted of calcium carbonate, that it, which includes at least 50%, or at least 60%, or at least 70%, or at least 80%, or at least 90%, or at least 95%, or about 100%, by weight, calcium carbonate.

The term "calcium carbonate" as used herein, refers to the chemical compound $CaCO_3$. In some embodiments, the calcium carbonate is solid calcium carbonate, which can be in crystalline or amorphous form. As used herein, crystalline forms of calcium carbonate include aragonite, calcite, ikaite, vaterite and monohydrocalcite. Other solid forms of calcium carbonate include amorphous calcium carbonate (ACC).

Calcium carbonate-containing material usable in the context of the present embodiments can be obtained or derived from natural sources (e.g., from living species or geological matter), or be synthetic (chemically synthesized). Commercially available forms of calcium carbonate are also encompassed.

Natural sources of calcium carbonate include, but are not limited to, rock formations, such as limestone, chalk, marble, travertine and tufa, as well as other geological matters. Calcium carbonate is also a principle structural component of many life forms, and thus can be obtained from, inter alia, corals, plankton, coralline algae, sponges, brachiopods, echinoderms, bryozoa, mollusks and other calcium carbonate-containing organisms.

In some of any of the embodiments described herein, the calcium carbonate-containing material comprises one or more forms of crystalline calcium carbonate.

In some of any of the embodiments described herein, the calcium carbonate-containing material comprises, or consists of, one or more forms of aragonite, calcite, ikaite, vaterite, and monohydrocalcite.

In some of any of the embodiments described herein, the calcium carbonate-containing material comprises aragonite. As used herein, the term "aragonite" refers to the crystalline form of calcium carbonate, which can be commonly found in as mineral deposits in caves and in oceans, and in the shells of mollusks and exoskeleton of cold and warm-water corals. The aragonite can be a geological aragonite or a biogenic aragonite (derived from living species such as corals or mollusks). Geological aragonite typically has a crystalline structure that is different from biogenic aragonite.

In some of any of the embodiments described herein, the calcium carbonate-containing material comprises calcite. As used herein, the term "calcite" refers to a crystalline form of calcium carbonate, differing from aragonite in its crystal lattice form, which can be obtained from sedimentary rocks and from the shells of some marine organisms.

In some of any of the embodiments described herein, the calcium carbonate-containing material comprises both aragonite and calcite.

In some of any of the embodiments described herein, the calcium carbonate-containing material (e.g., aragonite) comprises a coral exoskeleton. The term "coral exoskeleton", as used herein, refers to the exoskeleton of marine madreporic corals or material derived therefrom. Natural coral (e.g., Porites) consists of a mineral phase, principally calcium carbonate, typically in the structural form of aragonite or calcite, with impurities, such as Sr, Mg and F ions, and an organic matrix. Thus, as used herein, "coral exoskeleton" includes calcium carbonate, e.g., in the form of aragonite or calcite, with or without additional components (minerals, organic and inorganic components) derived from or secreted by the living coral or life forms associated therewith.

The term "coral exoskeleton" is also referred to herein simply as "coral skeleton".

In some of any of the embodiments described herein, the calcium carbonate-containing material is derived from a coral and comprises a coral exoskeleton.

Coral exoskeleton can be a commercially available material (e.g., Biocoral™) and has been reported to be biocompatible and resorbable. Coral-derived material described as coralline HA prepared by hydrothermally converting the original calcium carbonate of the coral *Porites* in the presence of ammonium phosphate, maintaining the original interconnected macroporosity of the coral, is also commercially-available (Pro Osteon®, Interpore Cross). The high content calcium carbonate coral exoskeleton has been shown to be biocompatible and biodegradable at variable rates depending on porosity, the implantation site and the species.

In some of any of the embodiments described herein, the coral exoskeleton or materials comprising the same are derived from a coral. In some embodiments, the coral can comprise any species, including, but not limited to, *Porites, Stylophora, Acropora, Millepora*, or a combination thereof.

In some embodiments, the coral is from the *Porites* species. In some embodiments, the coral is *Porites Lutea*.

In some embodiments, the coral is from the *Acropora* species. In some embodiments, the coral is *Acropora grandis* (which in one embodiment is very common, fast growing, and easy to culture). *Acropora* samples can be easily collected in sheltered areas of the coral reefs and/or can conveniently be cultured.

In some embodiments, the coral is from the *Millepora* species. In one embodiment, the coral is *Millepora dichotoma*. In one embodiment, the coral has a pore size of 150 microns and can be cloned and cultured, making *Millerpora* useful in the compositions and methods of this invention.

In some embodiments, the coral is from the *Stylophora* species. *Stylophora* is a genus of colonial stony corals in the family Pocilloporidae, commonly known as cat's paw corals or birdsnest corals. In some embodiments, the coral is *Stylophora subseriata*.

In another embodiment, the coral can be from any one or more of the following species: *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora solitaryensis; Acropora* cf *spicifera* as per Veron; *Acropora* cf *spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipore platyphylla; Monastrea curta; Monastrea colemani; Montipora caliculata; Montipora capitata; Montipora foveolata; Montipora meandrina; Montipora tuberculosa; Montipora* cf *vietnamensis; Oulophyllia laevis; Oxypora crassispinosa; Oxypora lacera; Pavona bipartita; Pavona venosa; Pectinia alcicomis; Pectinia paeonea; Platygyra acuta; Platygyra pini; Platygyra* sp "green"; *Platygyra verweyi; Podabacia* cf *lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata; Stylophora contorta; Stylophora danae; Stylophora kuehlmanni; Stylophora madagascarensis; Stylophora mamillata; Stylophora pistillata; Stylophora subseriata; Stylophora wellsi*, or any coral known in the art, or a combination thereof.

Coral exoskeleton is typically porous. In some embodiments, the calcium carbonate-containing material comprises coral exoskeleton having an average pore size (e.g., average diameter) in the range of from 1 micron to 1 millimeter. In one embodiment, the average pore size of a coral ranges from 1 to 200 microns. In one embodiment, the average pore size of a coral ranges from 30 to 180 microns. In one embodiment, the average pore size of a coral ranges from 50 to 500 microns. In one embodiment, the average pore size of a coral ranges from 150 to 220 microns. In one embodiment, the average pore size of a coral ranges from 250 to 1000 microns.

For most therapeutic applications, it is desirable that the calcium carbonate-containing material, when derived from natural sources, such as coral, be devoid of any cellular debris or other organisms associated therewith in its natural state. Thus, in some of any of the embodiments described herein, the coral exoskeleton is an acellular coral exoskeleton.

Calcium carbonate-containing material such as, for example, aragonite, may be a commercially-available material or can be prepared from coral or coral fragments, or from coral sand. Briefly, the coral can be prepared as follows: in one embodiment, coral or coral sand is purified from organic residues, washed, bleached, frozen, dried, sterilized and/or a combination thereof prior to use in the compositions and/or methods of the present embodiments.

In some of any of the embodiments described herein, preparation of the aragonite or coral exoskeleton includes contacting solid coral exoskeleton of a desired size and shape with a solution comprising an oxidizing agent, and washing and drying the solid material.

In some of any of the embodiments described herein, the oxidizing agent may be any suitable oxidizing agent, which facilitates the removal of organic debris from the coral exoskeleton. In some embodiments, the oxidizing agent is sodium hypochlorite.

According to this aspect, and in some embodiments, the process comprises conducting said contacting under mildly acidic conditions, so as to remove organic residues and provide acellular coral exoskeleton.

The calcium carbonate-containing material according to some embodiments of the present invention can be provided in a variety of forms, shapes and structures, compatible with a desired application. Some suitable forms and shapes include, but are not limited to, layers, blocks, spherical and hollow spherical forms, concentric spheres, rods, sheets, symmetrical and asymmetrical forms, amorphous and other irregular shapes and particles. The calcium carbonate-containing material can be shaped, for example, to fit a particular cavity or surface of tissue, or to fit an article containing the composition as described in further hereinafter.

In some of any of the embodiments described herein, the calcium carbonate-containing material is provided as particulate calcium carbonate-containing material.

In some embodiments, the particulate material comprises particles having an average particle diameter in the range of from 0.1 micron to 10 millimeter, or from 0.1 micron to 1 millimeter, or from 0.1 micron to 500 microns, or from 0.5 microns to 500 microns, or from 1 micron to 500 microns, or from 5.0 microns to 500 microns, including any subranges and intermediate values therebetween.

In some of any of the embodiments described herein, a calcium carbonate-containing material is produced from coral or coral sand according to a process comprising washing ground solid calcium carbonate (e.g. aragonite), such as coral or naturally occurring coral sand with water to desalinate it, then disinfecting and drying the desalinated coral sand at temperatures of about 80 degrees to about 150 degrees C., preferably 90 degrees to 120 degrees C., cutting larger pieces of coral into small pieces, and grinding the disinfected and dried coral or coral sand into small particles, including but not limited to particles of a size ranging from 5 to 500 microns. In some embodiments, coral is ground into particles having a particle diameter of in the range of 1-5, 1-20, 1-50, 1-100, 5-10, 10-15, 15-20, 10-50, 10-100, 20-100, 50-100, 80-150, 100-200, 100-350 or 150-500 microns across, and a particle volume in the range of 1-100, 50-500, 250-1000, 500-2500, 1000-5000 and 2500-10,000 cubic micron to 0.01-0.1, 0.05-0.5, 0.5-0.75, 0.75-1.0, 1.0-2.0 and 1.0-5.0 cubic millimeters in volume.

As used herein, the term "citrate salt" describes a compound composed of a citrate ion and one or more cations. The citrate ion can be represented by the formula $C_6H_5O_7^{3-}$ or $C_3H_5O(COO)_3^{3-}$. The cation can be monovalent, divalent or trivalent cation, and the stoichiometry of the citrate ion is in accordance with the selected cation.

The cation can be $Na^+$, $K^+$, $Li^+$, $Mg^{+2}$, $Zn^{+2}$, $Fe^{+2}$, $Fe^{+3}$, and any other suitable cation. If the cation is a monovalent cation, such as, for example, sodium cation, the citrate salt comprises 3 cations, and is, for example, trisodium citrate.

In some of any of the embodiments described herein, other salts of multicarboxylic acids can be used as alternative, or in addition, to a citrate salt as described herein.

By "multicarboxylic acid" it is meant an organic compound featuring two, three or more carboxylic acid groups. For a non-limiting example, a multicarboxylic acid can be represented by R(COOH)n, with R being an alkyl, alkenyl, cycloalkyl, and/or aryl, and n being an integer of at least 2 (e.g., 2, 3, 4, 5, etc.). The alkyl, alkenyl, cycloalkyl, or aryl, can be further substituted by one or more other substituents, as described herein.

In some of any of the embodiments described herein, other calcium-chelating agents can be used as alternative, or in addition, to a citrate salt as described herein.

In some of any of the embodiments described herein, other anti-coagulants can be used as alternative, or in addition, to a citrate salt as described herein. In some embodiments, such anti-coagulants are those acting by effecting the formation of cross-linked fibrin. In some embodiments, such anti-coagulants are not acting by effecting platelet aggregation. In some embodiments, the anti-coagulant is other than heparin or similarly-acting anti-coagulants that effect platelet aggregation.

In some of any of the embodiment described herein, a ratio between a citrate salt (or any alternative compound (e.g., anti-coagulant) as described herein) and a calcium carbonate-containing material in the composition ranges from 10:1 to 1:300, or from 1:1 to 1:300, or from 1:1 to 1:200, or from 1:1 to 1:100, or from 1:1 to 1:10, by weight, including any intermediate value and subranges therebetween.

In some of any of the embodiments described herein, a relative amount of the citrate salt (or any alternative compound as described herein) is no less than 0.1%, or no less than 0.5% or no less than 1%, by weight, compared to the amount of the calcium carbonate-containing material.

The anti-hemorrhaging composition described herein can further comprise additional ingredients, which are aimed at improving or facilitating its preparation, application and/or performance. Such additional ingredients include, for example, anti-irritants, anti-foaming agents, humectants, deodorants, antiperspirants, preservatives, emulsifiers, occlusive agents, emollients, thickeners, penetration enhancers, colorants, propellants and/or surfactants, depending on the final form of the composition.

Representative examples of humectants that are usable in this context of the present embodiments include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

Representative examples of deodorant agents that are usable in the context of the present embodiments include, without limitation, 2,4,4'-trichloro-2'-hydroxy diphenyl ether, and diaminoalkyl amides such as L-lysine hexadecyl amide.

Suitable preservatives that can be used in the context of the present embodiments include, without limitation, one or more alkanols, parabens such as methylparaben and propylparaben, propylene glycols, sorbates, urea derivatives such as diazolindinyl urea, or any combinations thereof.

Suitable emulsifiers that can be used in the context of the present embodiments include, for example, one or more sorbitans, alkoxylated fatty alcohols, alkylpolyglycosides, soaps, alkyl sulfates, or any combinations thereof.

Suitable occlusive agents that can be used in the context of the present embodiments include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients, that can be used in the context of the present embodiments include, for example, dodecane, squalane, cholesterol, isohexadecane, isononyl isononanoate, PPG ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present embodiments include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, and mixtures thereof.

Suitable penetration enhancers usable in context of the present embodiments include, but are not limited to, polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, menthol, TWEENS such as TWEEN 20, and the like. The permeation enhancer may also be a vegetable oil. Such oils include, for example, safflower oil, cottonseed oil and corn oil.

Suitable anti-irritants that can be used in the context of the present embodiments include, for example, steroidal and non steroidal anti-inflammatory agents or other materials such as menthol, aloe vera, chamomile, alpha-bisabolol, cola nitida extract, green tea extract, tea tree oil, licorice extract, allantoin, caffeine or other xanthines, glycyrrhizic acid and its derivatives.

Any of the additional ingredients or agents described herein is preferably selected as being compatible with the calcium carbonate-containing material and the citrate as described herein, such that there is no interference with the availability of these materials in the composition.

Any of the additional ingredients described herein is further preferably selected as being biocompatible.

In some embodiments, the anti-hemorrhaging composition further comprises an additional therapeutically active agent, for example, an additional hemostatic agent or composition or article, or, for example, an agent capable of disinfecting the treated area (e.g., antiseptic agents or compositions).

The composition described herein can be used per se, or can be formulated together with a pharmaceutically acceptable carrier.

As used herein, the term "pharmaceutically acceptable carrier" describes a carrier or a diluent that is used to facilitate the administration of the composition and which does not cause significant irritation to an organism and does not abrogate the biological activity and properties of the administered active materials. Examples, without limitations, of carriers include water, buffered aqueous solutions, propylene glycol, emulsions and mixtures of organic solvents with water, as well as solid (e.g. powdered or polymeric) and gaseous carriers.

Techniques for formulation and administration of drugs may be found in "Remington's Pharmaceutical Sciences" Mack Publishing Co., Easton, Pa., latest edition, which is incorporated herein by reference.

Compositions for use in accordance with the present embodiments thus may be formulated in conventional manner using one or more pharmaceutically acceptable carriers, excipients and/or auxiliaries, which facilitate processing of the compounds into preparations which can be used pharmaceutically. The dosage may vary depending upon the dosage form employed and the route of administration utilized.

The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutically acceptable carrier can be either an organic carrier or an aqueous carrier. In some embodiments, the carrier is an aqueous carrier. An aqueous carrier preferably comprises injectable-grade water, i.e., USP grade "water for injection". However, other forms of purified water may be suitable, such as, for example, distilled and deionized water.

Aqueous formulations are preferred since these formulations are gentle to bodily tissues and are suitable for use on injured blood vessels or tissues. Additionally, the water-insolubility of the calcium carbonate-containing material as described herein may account for its coagulation inducing and/or anti-hemorrhaging activity. However, non-aqueous formulations are also contemplated. For example, in cases where the composition is in a form of a paste or an emulsion, non-aqueous carriers or mixed carriers of aqueous and organic carriers can be used.

The composition may be formulated for administration in either one or more of routes, depending on the area to be treated.

According to some embodiments, the composition is formulated for topical application, as a topical dosage form.

As used herein, the phrase "topical dosage form" describes a dosage form suitable for topical administration to the treated area (e.g., an injured blood vessel or tissue). By "topical administration" it is meant application onto the treated area, or "local administration", whereby the treated area can be, for example, an internal or external injured blood vessel or tissue.

The compositions described herein can be, for example, in a form of a powder, granules, a cream, an ointment, a paste, a gel, a lotion, a milk, a suspension, an aerosol, a spray, a foam, a gauze, a wipe, a sponge, a wound dressing, a pledget, a patch, a pad, an adhesive bandage, and a non-adhesive bandage.

In some embodiments, the composition is formulated as a liquid reservoir, to be applied as drops, spray, aerosol, liquid, foam and the like. Suitable carriers and other ingredients are used in these cases. For example, for application as an aerosol or foam, a propellant is used. For application as foam, foam-forming agents can also be used.

In some embodiments, the composition is formulated as a cream. Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information. An exemplary cream formulation can be obtained by mixing the composition described herein with a carrier comprising cellulose derivatives such as cellulose acetate, hydroxyethyl cellulose and/or a polyethylene glycol.

In some embodiments, the composition is formulated as an ointment. Ointments are semisolid preparations, typically based on petrolatum or petroleum derivatives. The specific ointment base to be used is one that provides for optimum delivery for the active agent chosen for a given formulation. As with other carriers or vehicles, an ointment base should be inert, stable, nonirritating and nonsensitizing. As explained in *Remington: The Science and Practice of Pharmacy*, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

In some embodiments, the composition is formulated as a lotion. Lotions are preparations that are to be applied to the skin surface without friction. Lotions are typically liquid or semiliquid preparations in which solid particles, namely, the calcium carbonate-containing material particles, are present in a water or alcohol base. Lotions are typically preferred for covering/protecting large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

In some embodiments, the composition is formulated as a paste. Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

In some embodiments, the composition is formulated as a gel. Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

In some embodiments, the composition is formulated as a spray. Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery, the carrier evaporates, leaving concentrated active agent at the site of administration.

In some embodiments, the composition is formulated as a foam. Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the treated area, quickly evaporates, driving the active ingredient to the site of treatment.

In some embodiments, the composition is formulated as a powder or granules. Such compositions can be prepared by mixing the solid citrate salt and particulate calcium carbonate-containing material, and optionally forming granules or beads containing these ingredients, for example, by adding suitable agents (e.g., water soluble film-forming agents).

In some embodiments, a topical dosage form includes a substrate, e.g., a gauze, a wipe, a bandage, a pad, a pledget, a sponge, a mesh, a fabric, and the likes, and the calcium carbonate-containing material is incorporated in and/or on the substrate.

In some of these embodiments, the citrate is also incorporated in and/or on the substrate. In other embodiments, the citrate is individually provided together with the topical dosage form of the calcium carbonate-containing material. Such embodiments are discussed in further detail hereinbelow.

The substrate in such topical dosage forms can be of any form and materials used to make up gauzes, wipes, bandages, pads, pledgets, sponges, meshes, fabrics (woven and non-woven, cotton fabrics, and the like), and any other substrates commonly used in medical applications.

Such topical dosage forms may optionally further comprise an adhesive, for facilitating the topical application of the composition onto the treated area for a prolonged time period.

The calcium carbonate-containing material as described herein can be adhered to a surface of the substrate by adhesives, such as medically acceptable bioadhesives, polymer glues, etc., and can be applied to the substrate by, for example, dip coating with an adhesive base. Such dip coating can be effected during manufacture of the substrate, or at any time prior to its application. In some embodiments, the calcium carbonate-containing material, being a rigid, crystalline structure, can be embedded within and/or on the material of the substrate, for example, embedded into or onto a polymer or fabrics by application of heat, or fused to the substrate. In other embodiments, the calcium carbonate-containing material can be incorporated into the base material of the substrate, for example, mixed within the components of a polymer before polymerization, or mixed with components forming fibers used to make up a gauze or a mesh or pad, etc.

Compositions of the present invention may, if desired, be presented in a pack or dispenser device, such as an FDA (the U.S. Food and Drug Administration) approved kit, which may contain one or more unit dosage forms containing the active ingredient. The pack may comprise, for example, glass or plastic foil. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions of the invention formulated in a compatible pharmaceutical carrier may also be prepared, placed in an appropriate container, and labeled for a medical indication, as detailed herein.

The compositions described herein may be packed or presented in any convenient way. For example, they may be packed in a tube, a bottle, a dispenser, a squeezable container, or a pressurized container, using techniques well known to those skilled in the art and as set forth in reference works such as Remington's Pharmaceutical Science 15$^{th}$ Ed. It is preferred that the packaging is done in such a way so as to minimize contact of the unused compositions with the environment, in order to minimize contamination of the compositions before and after the container is opened.

The compositions described herein are preferably supplied in the concentration intended for use but may also be prepared as concentrates that are diluted prior to use. For example, concentrates requiring dilution ratios of 2:1 to 10:1 parts carrier (e.g., water) to a concentrate are contemplated.

In some embodiments, the composition described herein is packaged in a packaging material and identified in print, in or on the packaging material, for use in inducing blood coagulation and/or in reducing or arresting hemorrhaging, as described herein.

Articles-of-Manufacturing:

According to an aspect of some embodiments of the present invention, an article-of-manufacturing is provided, which comprises the composition as described herein in any of the respective embodiments, and any combination thereof, and means for topically applying the composition onto the treated area. In some embodiments, the article-of-manufacturing is configured to apply the composition to an injured blood vessel or tissue.

In some embodiments, the article-of-manufacturing comprises the composition as described herein, in a form of a suspension, packaged in a container, and means for applying the composition as drops, spray, aerosol, foam, using techniques well known to those skilled in the art and as described herein.

In some embodiments, the article-of-manufacturing comprises the composition as described herein, in a form of a cream, lotion, paste, ointment, and the likes, packaged in a suitable container, and optionally comprising means for dispensing the composition from the container.

In some embodiments, the article-of-manufacturing comprises the composition as described herein, in a form that comprises a powder or granules, packaged in a suitable container, and optionally comprising means for dispensing the composition from the container.

In some embodiments, the article-of-manufacturing comprises the composition as described herein, incorporated in and/or on a substrate, as described herein. The composition can be packaged in a sterile packaging.

The article-of-manufacturing can be labeled as described herein, for example, by being identified in print, in or on the packaging material, for use in inducing blood coagulation and/or reducing or arresting hemorrhaging, as described herein.

Kits:

According to an additional aspect of embodiments of the invention there is provided a kit, which comprises the composition described herein, being packaged in a packaging material.

The kit can be labeled, for example, by being identified in print, in or on the packaging material, for use in inducing blood coagulation and/or reducing or arresting hemorrhaging, as described herein.

The components of the composition can be packaged within the kit either together, as a single, ready for use, composition, or at least one of the components can be packaged individually. When one or more components are packaged individually, the kit may further be supplied with instructions indicating the route of preparing an anti-hemorrhaging composition, or otherwise indicating how to apply the components so as to contact an area to be treated with the composition. Such instructions can be, for example, mixing the components prior to application or simultaneously or subsequently applying the components onto an area to be treated.

In an exemplary embodiment, the kit comprises the calcium carbonate-containing material and the citrate (and/or an alternative compound as described herein) packaged together, optionally with other ingredients, in a first container, and a carrier (e.g., an aqueous carrier) packaged individually (e.g., in another container), and instructions to add the carrier to the first container, prior to application of the composition to the area to be treated, or vice versa (instructions to add the content of the first container to the carrier in the second container). The first (or second) container can be configured to apply the composition as drops, spray, aerosol, foam, etc.

In another exemplary embodiment, the kit comprises the calcium carbonate-containing material and the citrate packaged individually. For example, one of the calcium carbonate-containing material and the citrate is packaged in a first container optionally together with a first carrier suitable for the selected dosage form, as described herein, and the other component is packaged in a separate container, optionally together with a carrier, which can be the same as or different from the first carrier, if present, and the kit comprises instructions to mix the components in one of these containers (e.g., the first container) prior to application. Alternatively, the kit may comprise instructions to apply the components in the first and second containers, either simultaneously or sequentially.

By "simultaneously" it is meant application of the components at the same time, namely, such that both components contact the area to be treated within less than 1 minute.

By "sequentially" it is meant that components of one of the first and second container are applied to the area to be treated and then, within a time interval of from 1 to 10 minutes, or from 1 to 5 minutes, or from 1 to 2 minutes, the components of the other one of the first and second container are applied to the area to be treated.

In some embodiment, the instructions are for applying the calcium carbonate-containing material prior to applying the citrate salt, and optionally the second carrier.

In another exemplary embodiment, the kit comprises the calcium carbonate-containing material incorporated in and/or on a substrate as described herein, optionally packaged in a sterile packaging, and a separately-packaged composition comprising the citrate formulated, for example, with a carrier (e.g., an aqueous solution), or as a powder. The kit can comprise instructions to apply the citrate salt to the substrate prior to its application or to apply the citrate salt and the calcium carbonate-containing substrate to the treated area simultaneously or sequentially, in any order, to thereby contact the treated area with a composition as described herein.

The containers, substrates, and compositions included in the kit can be in accordance with any of the embodiments described herein, and any combination thereof.

Uses:

As demonstrated in the Examples section that follows, it has been uncovered, by serendipity, that a composition as described herein is capable of inducing blood coagulation within a short time period, whereby the blood clots formed upon coagulation are preserved, namely, do not dissolve or de-coagulate, for a few hours.

As used herein, the term "coagulation of blood" or "blood coagulation" describes clot formation in blood, namely, the formation blood clots in a subject's plasma. The clot formation can result from either or both of the intrinsic cascade, initiated when contact is made between blood and exposed negatively charged surfaces, and the extrinsic pathway, initiated upon vascular injury, leading to activation of factor X to Xa which hydrolyzes and activates prothrombin to thrombin. Thrombin then activates factors XI, VIII and V, until ultimately fibrinogen is converted to fibrin and factor XIII to XIIIa. Factor XIIIa (also termed transglutaminase) cross-links fibrin polymers solidifying the clot. Thus, as used herein, the term "clot" or "thrombus" refers to the final product of the blood coagulation step in hemostasis. There are two components to a clot/thrombus: aggregated platelets that form a platelet plug, and a mesh of cross-linked fibrin protein. The substance making up a thrombus is also known as cruor.

In some embodiments of the present invention, the blood is mammalian blood. In some embodiments, the blood is human blood.

The "inducing coagulation of blood", as used in the context of embodiments of the present invention, describes inducing coagulation and/or influencing the coagulation state of blood by increasing coagulation or coagulation rate of the blood. As such, the compositions described herein are characterized by increasing the clotting of blood and blood clotting state, which includes increasing clotting of plasma or increasing clotting rate of plasma, as well as reducing or preventing or decreasing a rate of lysis or dissolution of a blood clot.

By "clotting" it is meant formation of blood clots. By "clotting rate" or "coagulation rate", it is meant the percent of unclotted blood that turns into clotted blood within a certain time frame.

Clotting of blood and/or a rate of blood clots formation can be monitored in a variety of assays known in the art.

Exemplary techniques used in such assays include clot-based tests, chromogenic or color assays, direct chemical measurements, and ELISAs, are used for coagulation testing. An exemplary assay is the aPTT (activated partial thromboplastin time), performed by adding a surface activator (e.g., kaolin, celite, ellagic acid, or silica) and diluted phospholipid (e.g., cephalin) to citrated plasma. After incubation to allow optimal activation of contact factors (factor XII, factor XI, prekallikrein, and high-molecular-weight kininogen), calcium is added, and the clotting time is measured through absorbance. Clot-based assays use mostly citrated plasma, and the end point for all of them is fibrin clot formation.

In some embodiments, the compositions described herein can reduce the clotting time of human plasma and/or increase the clotting rate of human plasma.

According to some embodiments of the present invention, the composition as described herein is capable of inducing blood coagulation (blood clots formation) upon contacting the blood for a time period of a few minutes, for example, of 10 minutes or less, e.g., 9, 8, 7, 6, 5, 4 minutes or less, regardless of the blood's volume.

According to some embodiments of the present invention, the composition as described herein is such that upon contacting the blood, e.g., for a time period as described herein, at least 50% of a blood sample turns into blood clots.

According to some embodiments of the present invention, at least 50% of the clotted blood (formed upon contacting the composition as described herein) remains clotted for at least one hour, or for at least 2 hours, or for at least 4 hours, or more.

Any of the compositions, articles and kits described herein can therefore be used for inducing blood coagulation in a subject in need thereof.

As used herein, the term "subject" includes mammals, preferably warm-blooded mammals including birds, cows, horses, goat, sheep, pigs, dogs, cats, chickens and turkeys, and more preferably human beings at any age which suffer from a pathology that requires induction of blood coagulation.

According to an aspect of some embodiments of the present invention, there is provided a method of inducing blood coagulation, which is effected by contacting the blood with a composition as described herein.

The contacting can be effected in vitro or ex vivo for example, by contacting a blood sample with a composition as described herein.

The contacting can alternatively be effected in vivo, by contacting a blood of a subject with a composition as described herein.

According to an aspect of some embodiments of the present invention, there is provided a use of a composition as described herein for inducing coagulation of blood. Inducing blood coagulation can be effected in vitro, ex vivo, or in vivo, as described herein.

According to an aspect of some embodiments of the present invention there is provided a use of the composition as described herein in the manufacture of a medicament for inducing coagulation of blood in a subject in need thereof.

According to some of any of the embodiments described herein for the methods and uses of the compositions described herein, the contacting is effected such that at least 50% of the blood is clotted upon contacting with the composition for less than 10 minutes (e.g., for 4-5 minutes).

According to some embodiments of the present invention, the contacting is effected such that at least 50% of the clotted blood formed upon said contacting remains clotted for at least one hour, as described herein.

According to some of any of the embodiments described herein for the methods and uses of the compositions described herein, the contacting is effected by applying the composition, or an article-of-manufacturing containing same, to an injured blood vessel.

The injured blood vessel can be an internal or external blood vessel, and can form a part of an injured tissue or organ.

The term "tissue" refers to part of an organism consisting of cells designed to perform a function or functions. Examples of tissue include, but are not limited to, skin tissue, hepatic tissue, pancreatic tissue, blood tissue, cardiac tissue, gastrointestinal tissue, vascular tissue, renal tissue, pulmonary tissue, gonadal tissue, hematopoietic tissue, nervous tissue, abdominal tissue, and spleen tissue.

When contacting is effected in vivo, the composition is preferably administered in a direct, local manner, for example, via placement or application (e.g., by injection) of the composition, or an article-of-manufacturing containing same, directly into or onto an injured tissue region of a subject.

In some of any of the embodiments described herein, contacting blood with the composition, or an article-of-manufacturing containing same, as described herein is effected such that an effective amount of the composition is contacted with the blood (e.g., an injured blood vessel or tissue, also referred to herein as an area to be treated).

By "effective amount" it is meant an amount that induces blood coagulation by turning at least 50% of the blood that contacts the composition into blood clots within no more than 30 minutes, or no more than 20 minutes, or no more than 10 minutes, or within a shorter time period (e.g., 4-5 minutes). In some embodiments, an "effective amount" of the composition as described herein is further an amount that is such that at least 50% of the clotted blood remains clotted for at least one, two or more hours.

In exemplary, non-limiting embodiments, an effective amount of a composition as described herein is such that an amount of a citrate salt ranges from 0.1% to 1%, or from 0.3% to 0.4%, by weight, per ml blood that contacts the composition, and an amount of the calcium carbonate-containing material ranges from 0.1 to 200 mg per ml blood that contacts the composition.

The contacting of the injured blood vessel or tissue with the composition, or an article-of-manufacturing containing same, can be effected while using any of the articles-of-manufacturing or kits as described herein. Depending on the form of the composition, contacting an injured blood vessel or tissue with the composition can be effected such that the contacting with the calcium carbonate-containing material and the citrate salt can be effected simultaneously or sequentially, as described herein.

Any of the compositions, articles, kits, methods and uses described herein for inducing blood coagulation can be efficiently utilized for reducing or arresting hemorrhaging in a subject in need thereof.

The hemorrhaging can be an external or, preferably, an internal hemorrhaging.

Accordingly, the compositions and methods described herein can be used for treating hemorrhaging, e.g., internal hemorrhaging, in a subject in need thereof, by contacting an injured blood vessel or tissue of the subject with a composition as described herein.

In some embodiments, the contacting is effected outside a medical facility (e.g., a hospital), for example, at a site where trauma has occurred, as an emergency treatment. In some embodiments, treating hemorrhaging is followed by a surgical procedure, e.g., by procedures well known in the art.

In some embodiments, the contacting is effected during a surgical procedure, to assist is arresting hemorrhaging as a result of a trauma or as a result of the surgical procedure itself.

In some embodiments, any of the compositions, methods and uses described herein for inducing blood coagulation are utilized for inducing blood coagulation in subjects suffering from a disease or disorder in which increasing blood clots formation or increasing a rate of blood coagulation is desired. Such diseases and disorders include, for example, hemophilia, dialysis treatments, damage control during operations and patients using anti-coagulants.

It is expected that during the life of a patent maturing from this application many relevant calcium carbonate-containing materials and/or citrate salts will be developed and the scope of the terms "carbonate-containing material" and "citrate salt" is intended to include all such new technologies a priori.

As used herein the term "about" refers to ±5% or ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "alkenyl" group refers to an unsaturated group corresponding to an alkyl group (as defined herein) which consists of at least two carbon atoms and at least one carbon-carbon double bond.

An "alkynyl" group refers to an unsaturated group corresponding to an alkyl group (as defined herein) which consists of at least two carbon atoms and at least one carbon-carbon triple bond.

A "cycloalkyl" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, phosphate, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein. Representative examples are piperidine, piperazine, tetrahydrofuran, tetrahydropyran, morpholine and the like.

As used herein, the terms "amine" and "amino" refer to either a —NR'R" group or a —N$^+$R'R"R'" group, wherein R', R" and R'" are each independently hydrogen, alkyl, alkenyl, alkynyl, cycloalkyl, heteroalicyclic (bonded through a ring carbon), aryl and heteroaryl (bonded through a ring carbon). Optionally, R', R" and R'" are each independently hydrogen or alkyl comprising 1 to 4 carbon atoms. Optionally, R' and R" are hydrogen.

An "oxo" group refers to a =O group.

A "halo" group refers to a fluorine, chlorine, bromine or iodine atom.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "nitro" group refers to an —NO$_2$ group.

A "cyano" or "nitrile" group refers to a —C≡N group.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

A "carboxy" or "carboxyl" encompasses both C-carboxy and O-carboxy groups, as defined herein.

A "carboxylic acid" refers to a C-carboxy group wherein R' is hydrogen or to a compound comprising such a group.

A "sulfinyl" group refers to an —S(=O)—R' group, where R' is as defined herein.

A "sulfonyl" group refers to an —S(=O)$_2$—R' group, where R' is as defined herein. A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR"— group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

A "urea' group refers to an —N(R')—C(=O)—NR"R'" group, where each of R', R" and R'" is as defined herein.

The term "thiourea" describes a —N(R')—C(=S)—NR"— group, with each of R' and R" as defined hereinabove.

The term "phosphonyl" or "phosphonate" describes a —P(=O)(OR')(OR") group, with R' and R" as defined hereinabove.

The term "phosphinyl" describes a —P(=O)R'R" group, with R' and R" as defined hereinabove.

The term "phosphate" describes an —O—P(=O)(OR')(OR") group, with each of R' and R" as defined hereinabove.

The term "hydrazine" describes a —N(R')—N(R")R'" group, with each of R', R" and R'" as defined hereinabove.

The terms "comprises", "comprising", "includes", "including", "having" and their conjugates mean "including but not limited to".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

MATERIALS AND EXPERIMENTAL METHODS

Materials:

Geological aragonite and amorphous calcium carbonate were obtained from Alfa Aesar.

Glass beads (0.1 mm diameter) were obtained from BIO-SPEC.

7% hypochlorite solution was obtained from CARLO ERBA reagents.

$H_2O_2$ solution (Gerdrogen 30% by weight) was obtained from Riedel-de Haen, Germany.

Trisodium citrate was obtained from baker analyzed.

All other chemicals were obtained from known vendors.

Preparation of Coral Skeleton Particles:

Coral skeleton particles were prepared from the scleractinian corals *Porites lutea* and *Stylophora subseriata*. Coral cores were drilled out from long-lived massive colonies, were cut into small pieces (between about 0.25 and about 1 cm$^3$) and bleached with a 7% commercial hypochlorite solution. Samples were then rinsed with distilled water and dried in air. The organic matter was removed from the samples by washing with 2M NaOH solution, followed by washing with analytic $H_2O_2$ solution (Gerdrogen 30% by weight) for further removal of organic deposits, and were thereafter sterilized in an autoclave (128° C., 40 minutes).

The obtained coral skeleton particles were further grained manually, using a marble mortar and pestle, or a grainer device, to obtain particulates featuring a length ranging from about 5 to about 500 microns.

Blood Coagulation Assay:

Rats or mice (2-3 months old) were sacrificed using $CO_2$ and their blood was extracted directly from the heart using 1 ml syringe and a 23-gauge needle. Blood was transferred to two groups of experimental tubes (400 microliters in each): empty tubes, and tubes containing citrate at a final concentration of 0.35% by weight (e.g., 50 μl of a respective 3.2% stock solution of trisodium citrate in water).

The anti-coagulant activity of the citrate powder was confirmed by recording absence of clot formation during the entire experiment, and thereafter, each of the following components was added to the tubes in both groups, at varying amounts:

=Coral skeleton particulates prepared from *Porites lutea* (to achieve a final concentration of 50-200 mg/ml)

=Coral skeleton particulates prepared from *Stylophora subseriata* (to achieve a final concentration of 50-200 mg/ml)

=Geological aragonite (to achieve a final concentration of 50-200 mg/ml)

=amorphous calcium carbonate (ACC) (1-200 mg, to achieve a final concentration of 2-50 mg/ml)

=Glass beads (0.1 mm diameter; to achieve a final concentration of 100 mg/ml)

Coagulation and anti-coagulation activity (presence and absence, respectively, of blood clots) was observed using a CCD camera.

Experimental Results

As discussed hereinabove, it has been previously uncovered that exposure of mouse blood to particles of coral exoskeleton in vitro results in strong reduction of coagulation. See, PCT/IL2015/050447.

While investigating whether the anti-coagulation effect of the coral exoskeleton is altered by the presence of other anti-coagulates, particulate coral exoskeleton was added to citrate-containing blood. Surprisingly, while citrate by itself blocked clotting, as expected, the addition of coral exoskeleton particles obtained from different types of corals caused coagulation, despite the presence of citrate.

Reference is made to FIG. 1A, which presents an image of blood drawn from mice, in the presence of 0.35% by weight of citrate, and shows the anti-coagulation effect of the citrate; and to FIG. 1B, which presents an image of blood drawn from mice, in the presence of 0.35% by weight of citrate, 5 minutes after the addition of particulate exoskeleton of the coral *Stylophora subseriata* to the citrate-containing blood at a final concentration of 50 mg/ml.

In order to test whether the pro-coagulation activity is a result of the unique crystalline features of coral skeletons, the effect of geological aragonite, a commercially available coral skeleton that is not derived from an animal source was tested. Geological aragonite is a form of crystalline calcium carbonate which preserves the aragonite structure but lacks the coral skeleton porous shape.

FIGS. 2A-C present the effect of geological aragonite on coagulation of citrate-containing blood drawn from mice. FIG. 2A shows the blood clot formed 5 minutes upon addition of geological aragonite, at a final concentration of 50 mg/ml to citrate-containing (0.35% by weight) blood. FIG. 2B presents a higher magnification of FIG. 2A, showing the jell-shaped clot (left arrow) formed near crystals of geological aragonite (right arrow). FIG. 2C shows that the formed gel is rigid and preserves its shape even when stretched against gravity.

The obtained results show that the effect of the geological aragonite on coagulation surpassed that of the corals skeleton and caused jellification of the blood. The gel incorporated most of the blood liquid and was structurally stable even when stretched against gravity. The clot remained un-dissolved and stable for several hours and left no residues when moved around.

While further exploring the effect of the crystalline structure of calcium carbonate, citrate-containing blood drawn from mice was exposed to varying amounts of synthetic amorphous calcium carbonate (ACC), which lacks the aragonite crystalline structure. Images were taken 5 minutes upon exposure to ACC, and are presented in FIG. 3. As shown in FIG. 3, ACC induced blood coagulation in citrate-containing blood in a dose dependent manner. Tubes were loaded with 50 μl of a 3.2% sodium citrate and 400 μl of fresh blood, followed by addition of varying amounts of ACC particles (1-200 mg) in each tube. The clotting effect of ACC was observed at all the tested concentrations: from about 2 to about 50 mg/ml.

As a reference, the citrate-containing blood samples were exposed to potassium carbonate at a final concentration of 50 mg/ml. A slow coagulation (40-45 minutes) was observed (data not shown), suggesting that carbonate ions do not play a significant role in the coagulation activity.

The effect of calcium carbonate on coagulation was tested by replacing the citrate salt with another blood anti-coagulation agent—heparin. Blood drawn from mice was added to test tubes containing heparin (10-30 UPS/ml) and particulates of exoskeleton of *Stylophora* were added to the heparin-containing blood samples to achieve a final concentration of 100 mg/ml. FIG. 4 presents images of heparin-containing blood sample with particulate coral skeleton, 20 minutes upon addition, and without the coral skeleton, and show that the coral skeleton had no effect on coagulation.

Coagulation was not observed also when citrate-containing blood was exposed to glass beads (100 microns diameter) instead of calcium carbonate (data not shown).

In accordance with preliminary data obtained in a PPT assay, presented in FIG. 5, conducted with a citrate/aragonite composition as described herein, it has been suggested that a composition as described herein does not bind to a single factor involved in the intrinsic and extrinsic pathways of the coagulation mechanism but rather affects the formation of cross-linked fibrin in the presence of factor VIII.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A blood coagulation-inducing composition comprising a citrate salt and a calcium-carbonate containing material, the composition being formulated as a topical dosage form.

2. The composition of claim 1, wherein the calcium carbonate-containing material comprises crystalline calcium carbonate.

3. The composition of claim 1, wherein said calcium carbonate-containing material comprises a coral exoskeleton.

4. The composition of claim 1, wherein said calcium carbonate-containing material comprises acellular coral exoskeleton.

5. The composition of claim 1, wherein said calcium carbonate-containing material comprises aragonite.

6. The composition of claim 1, wherein said calcium carbonate-containing material comprises biogenic aragonite.

7. The composition of claim 1, wherein said calcium carbonate-containing material comprises geological aragonite.

8. The composition of claim 1, wherein the calcium carbonate-containing material comprises amorphous calcium carbonate.

9. The composition of claim 1, wherein said calcium carbonate-containing material is a particulate material.

10. The composition of claim 9, said particulate material comprises particles having an average particle diameter in the range of from 0.1 micron to 10 millimeter, or from 0.1 micron to 1 millimeter, or from 0.1 micron to 500 microns, or from 0.5 microns to 500 microns, or from 1 micron to 500 microns, or from 5.0 microns to 500 microns.

11. The composition of claim 1, wherein a weight ratio of said citrate and said calcium carbonate-containing material ranges from 10:1 to 1:300.

12. The composition of claim 1, being in a form of a powder, a gel, a spray, a foam, a mousse, an ointment, a paste, a lotion, a gauze, a wound dressing, a suspension, an adhesive bandage, a non-adhesive bandage, a wipe, a gauze, a pad, and a sponge.

13. An article-of-manufacturing comprising the composition of claim 1, the article-of-manufacturing being configured for applying the composition to an injured blood vessel and/or tissue.

14. A kit comprising the composition of claim 1.

15. The kit of claim 14, wherein the calcium carbonate-containing material and the citrate salt are packaged together within the kit.

16. The kit of claim 14, wherein the calcium carbonate-containing material and the citrate salt are packaged individually within the kit.

17. The kit of claim 14, comprising an article-of-manufacturing comprising the composition and configured for applying the composition to an injured blood vessel and/or tissue.

18. A method of inducing coagulation of blood, the method comprising contacting the blood with a composition that comprises a citrate salt and a calcium-carbonate containing material, said contacting comprising applying the composition to an injured blood vessel and/or tissue.

19. The method of claim 18, wherein said contacting comprises contacting the blood with an article-of-manufacturing comprising the composition and configured for applying the composition to said injured blood vessel and/or tissue.

20. The method of claim 18, wherein at least 50% of the blood is clotted upon contacting with the composition for less than 10 minutes.

21. The method of claim 18, wherein at least 50% of said clotted blood remains clotted for at least 2 hours.

22. The method of claim 18, wherein said contacting is effected in vivo.

23. The method of claim 18, wherein said blood vessel is an internal blood vessel or a blood vessel of an internal tissue.

24. A method of reducing or arresting hemorrhaging in a subject in need thereof, the method comprising contacting an injured blood vessel or tissue of the subject with a composition that comprises a citrate salt and a calcium-carbonate containing material.

25. The method of claim 24, wherein the hemorrhaging is an internal hemorrhaging.

* * * * *